United States Patent [19]

Staniforth et al.

[11] Patent Number: 5,470,603
[45] Date of Patent: Nov. 28, 1995

[54] ELECTROSTATIC COATING OF SUBSTRATES OF MEDICINAL PRODUCTS

[75] Inventors: John N. Staniforth; Martin P. Grosvenor, both of Bath, England

[73] Assignee: Hoechst UK Limited, Hounslow, United Kingdom

[21] Appl. No.: 937,870

[22] PCT Filed: Feb. 21, 1992

[86] PCT No.: PCT/GB92/00323
§ 371 Date: Oct. 19, 1992
§ 102(e) Date: Oct. 19, 1992

[87] PCT Pub. No.: WO92/14451
PCT Pub. Date: Sep. 3, 1992

[30] Foreign Application Priority Data

Feb. 22, 1991 [GB] United Kingdom ............... 9103711

[51] Int. Cl.⁶ ............................. A61K 9/28; B05B 5/08
[52] U.S. Cl. ................... 427/2.14; 427/2.18; 427/471; 427/485; 427/202; 427/212; 427/322; 427/346; 427/348; 427/536
[58] Field of Search ........................... 427/346, 348, 427/189, 194, 195, 212, 3, 202, 471, 485, 322, 536, 242, 461, 2.14, 2.18; 118/16, 20, 21, 22, 18, 63, 624, 632, 633

[56] References Cited

U.S. PATENT DOCUMENTS

| | | | |
|---|---|---|---|
| 1,226,824 | 5/1917 | Steely | 118/18 |
| 2,421,801 | 6/1947 | Miller | 118/20 |
| 2,555,519 | 6/1951 | Tolle et al. | 427/485 |
| 2,685,537 | 8/1954 | Dunmire | 118/20 |
| 3,323,933 | 6/1967 | Barford et al. | 427/485 |
| 3,536,034 | 10/1970 | Lecrone | 118/16 |
| 4,209,550 | 6/1980 | Hagenbach et al. | 427/27 |
| 4,495,217 | 1/1985 | Schrum | 427/27 |
| 4,510,170 | 4/1985 | Cosentino et al. | 427/33 |
| 4,702,932 | 10/1987 | Cosentino et al. | 427/33 |
| 4,724,154 | 2/1988 | Cosentino et al. | 427/27 |
| 4,774,102 | 9/1988 | Kiefer et al. | 427/28 |
| 4,811,689 | 3/1989 | Yamamoto et al. | 118/624 |
| 4,937,080 | 6/1990 | Appelgren et al. | 427/3 |
| 4,979,463 | 12/1990 | Sollich | 118/21 |
| 5,000,978 | 3/1991 | Davidson et al. | 427/212 |
| 5,015,501 | 4/1991 | Johnson | 427/242 |
| 5,132,142 | 7/1992 | Jones et al. | 427/196 |
| 5,178,874 | 1/1993 | Kwan et al. | 427/3 |

FOREIGN PATENT DOCUMENTS

| | | |
|---|---|---|
| 522840 | 12/1955 | Belgium . |
| 649491 | 10/1964 | Belgium . |
| 0085149 | 8/1983 | European Pat. Off. . |
| 0127376 | 12/1984 | European Pat. Off. . |
| 0148772 | 7/1985 | European Pat. Off. . |
| 0265376 | 4/1988 | European Pat. Off. . |
| 0381044 | 1/1990 | European Pat. Off. . |
| 0405884A1 | 1/1991 | European Pat. Off. . |
| 2636152 | 8/1976 | Germany . |
| 1123517 | 4/1967 | United Kingdom . |
| 1075404 | 7/1967 | United Kingdom . |
| 1449993 | 9/1976 | United Kingdom . |
| 2042930 | 10/1980 | United Kingdom . |
| 2056885 | 3/1981 | United Kingdom . |
| 2142468 | 2/1984 | United Kingdom . |
| 2177585 | 10/1986 | United Kingdom . |
| WO86/03993 | 7/1986 | WIPO . |

*Primary Examiner*—Diana Dudash
*Attorney, Agent, or Firm*—Nixon & Vanderhye

[57] ABSTRACT

Method of coating cores of pharmaceutical tablets with a dry powder, wherein the cores are fed onto a conveyor, the dry powder is supplied to a region through which the cores are to be conveyed, and the cores are conveyed on the conveyor through the region with the cores maintained at a different electric potential from the dry powder. In this way, the dry powder is attracted to the exposed surfaces of the cores to form powder coatings thereon. The dry powder on the surface of the cores is then melted to convert the powder into fused film coatings secured to the cores.

24 Claims, 2 Drawing Sheets

ELECTROSTATIC COATING OF SUBSTRATES OF MEDICINAL PRODUCTS

The present invention relates to a method and apparatus for electrostatic coating of substrates of medicinal products. The invention is particularly, but not exclusively, concerned with the coating of pharmaceutical tablet cores with a dry powder.

BACKGROUND OF THE INVENTION

Proposals for electrostatic coating of tablets have been made for at least the last thirty years or so. For example, GB-1075404 (published in 1967) proposes an apparatus for coating tablets in which a liquid is sprayed onto one face of each tablet core as the tablet cores are conveyed below a first stage sprayer having an associated high voltage grid, the coating is dried, the coated cores are then conveyed below a second stage sprayer having an associated high voltage grid with the other side of the tablets uppermost, and then that coating is dried again.

Various paper proposals for electrostatically coating tablet cores with a liquid or a dry powder have been made but as yet at least in the case of pharmaceutical tablets there is no recognized electrostatic coating method or apparatus that has proved sufficiently successful to be applied commercially on a reasonable scale. While there are rotary tablet presses capable of producing pharmaceutical tablet cores continuously at a rate of for example 5,000 tablets per minute, the subsequent coating of the tablet cores is most commonly carried out as a batch process by applying a liquid coating in a revolving drum.

In order to provide a commercially viable apparatus or method for coating medicinal products various problems must be overcome. It is in many ways easier to apply a liquid rather than a dry powder as the coating material and therefore, although both options have been considered in research, workers have favoured the use of liquids. If a dry powder is applied then it is harder to obtain adhesion of the coating to the substrate, which is not itself likely to be sufficiently electrically conducting, even when the powder is electrostatically charged. In order to provide a lasting bond between the substrate and the powder, the powder must be transferred into a film, for example by melting, but in the case of a medicinal product, which in many cases will include organic materials, must not be damaged. Furthermore an even coating is required and it is very difficult to obtain an even coating of powder on an electrically insulating medicinal substrate, even when the powder is electrostatically charged.

When liquid coating is used, the coating must be dried. Theoretically such drying could in some circumstances be carried out at room temperature but in commercial practice it is important, for example because of the rate at which the process must be carried out, to heat the tablets and that is expensive because of the large input of energy required to vapourize the solvent used in the liquid coating. Another disadvantage of liquid coating is that it cannot be used for coating materials that are not soluble or suitably dispersible in a usable liquid, preferably water.

DESCRIPTION OF THE INVENTION

It is an object of the invention to provide an improved method and apparatus for coating substrates of medicinal products.

According to the invention there is provided a method of coating substrates of medicinal products with a dry powder, the method including the following steps:

feeding the medicinal substrates onto a conveying means;

supplying the dry powder to a region through which the medicinal substrates are to be conveyed on the conveying means;

conveying the medicinal substrates on the conveying means through the region with the conveying means and/or the substrates maintained at a different electric potential from the dry powder, whereby the dry powder is attracted to the exposed surfaces of the substrates but is unable to reach the surfaces of the substrates in contact with the conveying means, and treating the dry powder coatings to convert the powder into a fused film secured to the substrates.

By placing the substrates on a conveying means during the charging process, it is found that a satisfactory spread of powder over the substrate can be obtained. It is also found that some unevenness of distribution is not necessarily serious, even if it is important for the final tablet to have a coating of substantially constant thickness, because further levelling can take place when the powder is converted into a fused film. Thus the present invention enables a desired thickness of coating to be applied uniformly over a surface of a substrate. The thickness of the coating will typically be greater than 10 μm. Although the present invention as defined above still involves the input of energy to convert the powder into a fused film, the amount of energy required can be substantially less than that involved in the case where a liquid coating comprising a coating substance dissolved in a suitable solvent is applied and the solvent has to be vapourised after application of the coating. The method also removes the necessity for solvent handling and disposal and for batch processing.

The medicinal products will usually be pharmaceutical tablets ("tablets" being as defined below) but they may also be implants that are not administered orally.

While reference is made throughout the specification to "tablets" and the invention is of particular application to pharmaceutical tablets of conventional shape, it should be understood that the term is to be interpreted in a broad sense as covering also, for example, pellets, capsules or spherules.

While the method of the invention will generally be applied to the coating of tablet cores (or substrates of the medicinal products) which have not received any coating since being formed in a press, it may be used to apply a coating on top of an already coated or partly coated tablet core.

The method of the present invention may be carried out as a continuous process. In practice there are considerable advantages in being able to operate the coating process continuously rather than as a batch process.

While there are certain applications, which will be referred to later, where it will be desired to coat the medicinal substrate on one side only or with at least one discontinuity in the coating, it will generally be desirable to coat all of the exterior of the tablet core. Accordingly the method preferably comprises the following further subsequent steps:

feeding the medicinal substrates onto a conveying means with the treated powder coatings of the substrates in contact with the conveying means and with that surface of the substrate that was in contact with the conveying means during the above-mentioned conveying step exposed;

supplying the dry powder with which the substrates are to be coated to a region through which the conveying means passes:

conveying the substrates on the conveying means through the region with the conveying means and/or the substrates maintained at a different electric potential from the dry powder whereby the dry powder is attracted to the exposed surfaces of the substrates but is unable to reach the coated surfaces of the substrates in contact with the conveying means, and treating the dry powder coatings to convert the newly applied powder into a fused film secured to the substrates.

For practical convenience the conveying means used during the second coating stage is preferably not the one used during the first coating stage but it is possible to use the same conveying means for both coating stages. The powder applied during each coating stage will usually be the same but it is of course possible to apply different powders at each stage; similarly the same thickness of coating will usually be applied at each stage but different thicknesses may be applied, if desired.

If desired still further coating stages may be employed for example to apply powder to sides of the products, if the sides have not already been coated.

Preferably the conveying means comprises a conveyor belt. The conveying means may however comprise an inclined static surface or a vibrated surface along which the substrates slide. The friction between the substrates and the inclined surface may be reduced by passing air through the inclined surface from the underside.

Converting the powder into a fused film may advantageously comprise converting the powder into the liquid phase after which it returns to the solid phase.

We have found that the conversion of the dry powder into a fused film not only serves to secure the coating to the substrate but also provides a means by which the distribution of the coating material over the substrate may be made more even. In some cases the coating material may have such a low viscosity when fused that the coating will distribute itself evenly over a substrate but in most cases the coating material will be more viscous and the method therefore preferably includes the further mechanical treatment of the coating to even out the depth of the coating over the surface of the substrate. The evening out step may be carried out by passing the substrates under a vibrating plate or a rotating roller, the plate or roller contacting and evening out the coating on the substrate. Alternatively the evening out step may be carried out by passing the substrates under a jet of air, for example an air knife, the curtain of air generated as the air knife evening out the coating on the substrate; the air may be heated in order to avoid premature solidifying of the coating.

The dry powder coating is preferably converted into a fused film by heating, preferably by infra red radiation, but other forms of electromagnetic radiation may be used. Also the conversion into a fused film may be achieved partly or wholly by reducing the pressure of the region. Usually the change in the coating upon heating will simply be a physical change from a powder to a liquid and then, on cooling, to a continuous solid coating, but there are other possibilities: for example, the powder coating may comprise a polymer which is cured during the treating step, for example by irradiation with energy in the gamma, ultra violet or radio frequency bands, to form a continuous cross-linked polymer coating.

It is preferable to charge the powder to an appropriate electric potential, which may be positive or negative. The powder is preferably charged as it is supplied to the region through which the conveying means passes. The charging may be carried out using a corona charging apparatus; another possibility is to charge the powder triboelectrically. One or more electrodes maintained at a selected potential which would normally be of the same sign as that of the powder (i.e. a positive potential if the powder is positively charged and a negative potential if the powder is negatively charged) are preferably provided above the conveying means in the region to which the powder is supplied. The positioning of the electrodes and the potential(s) at which they are maintained influences the electric field in the region and therefore the path of the powder through the region.

The conveying means is preferably maintained at a potential which is either earth potential or of opposite sign to the potential to which the powder is charged. The conveying means may have an electrically conducting upper surface on which the medicinal substrates rest. In most cases the substrates will be made of an electrically insulating material; they may be treated prior to application of the powder to make them more electrically conducting, for example by moistening the exterior of the substrate. Such moistening facilitates the maintenance of the exterior of the substrate at earth potential and thus facilitates the application of the powder to the core.

The method of the invention is not restricted to the use of any particular form of coating material. On the other hand, for good results, the dry powder preferably has the following physical properties:

(1) A particle size in the range of 1 μm to 1000 μm and preferably in the range of 30 μm to 80 μm; a small particle size enables the powder to be evenly dispersed in the region to which it is supplied and through which the conveyor belt passes.

(2) A relatively high resistivity in the range of $10^6$ Ωm to $10^{24}$ Ωm and preferably in the range of $10^{10}$ Ωm to $10^{14}$ Ωm; a high resistivity facilitates maintenance of the powder charge but makes it harder to charge the powder.

(3) A viscosity when in the liquid phase of less than 500 Pas and preferably less than 75 Pas; a low viscosity facilitates even spreading of the coating over the surface of the tablet core.

(4) After conversion to a fused film, a tensile strength of more than $0.5N/m^2$ and preferably more than $3.5N/m^2$; a reasonably strong and tough coating is required in order to protect the tablet during subsequent handling up to the administration of the tablet.

(5) A melting point which lies in the range of 50° C. to 180° C. and preferably 60° C. to 100° C. With a relatively low melting point less energy is required to convert the powder into the liquid phase and the risk of damage to the tablet core from heating is reduced. The latter point is of special importance when the drug in the tablet core is liable to be damaged if its temperature is increased substantially above room temperature.

Examples of materials which, alone or when blended with other materials, meet some or all of the five preferred properties listed above can be found in: polyamides, polyalkenes, waxes, oils, polyesters, sugar alcohols, sugars, polyoxyethylenes and ethylene vinyl acetate copolymer. Examples of suitable sugar alcohols are: sorbitol and xylitol. Examples of suitable sugars are sucrose and lactose. A polyester having properties especially suitable for the method of the invention is polycaprolactone.

The materials indicated above may be modified by blending other materials with them so as to improve their physical properties to match more closely the properties indicated above. One or more opacifiers, for example titanium dioxide, and/or colourants, for example aluminium lakes or dyes, may also be added to the formulation of the coating material.

The materials listed above fall into two categories: the water soluble materials (polyoxyethylenes, sugars, sugar alcohols) and the poorly soluble or insoluble polymeric materials. If a coating is required to dissolve quickly following administration, then a water soluble material will generally be preferred whereas if a delayed, controlled or modulated release of the drug is required a poorly soluble or insoluble polymeric material is likely to be advantageous.

An especially preferred sugar alcohol is xylitol, while an especially preferred polymeric material is a polyester, such as, for example polycaprolactone. In both cases, however, it may be desirable to add small quantities of other substances to improve the physical properties of the material.

In another aspect the present invention is not concerned exclusively with coating a substrate with a dry powder and provides a method of coating substrates of medicinal products including the following steps:

feeding the substrates onto a conveying means, providing an electrode spaced above the conveying means and extending along and across the conveying means to define a box-like region between the electrode and the conveying means, and maintaining the electrode at a first electric potential, supplying coating material to the box-like region and electrically charging the coating material to a second electric potential, conveying the substrates on the conveying means through the region with the conveying means and/or the substrates maintained at a different electric potential from the coating material and the electrode, whereby the coating material is attracted to the exposed surfaces of the substrates.

The invention may be used to apply a coating of controlled thickness and may be employed for a medicinal product containing a drug that is to be instantaneously released when administered or that is to be the subject of controlled or modulated release, such control or modulation being achieved from the nature of the coating and/or from the nature of the core. Where the desired form of release is to be achieved by characteristics of the coating, it may be preferred to leave one portion of the product uncoated or coated with a different material. In the case of a tablet having faces at opposite ends connected by a cylindrical side wall, the portion that is uncoated or coated with a different material may be one of the faces of the tablet, a small portion of one of the faces or a side wall of the tablet.

As has already been made clear, the methods described above have the advantage that they can be carried out continuously. They can therefore be employed as part of a continuous process for producing coated medicinal products, especially pharmaceutical tablets.

Thus, the present invention provides a continuous process for producing coated tablets comprising the steps of:

continuously forming pharmaceutical tablet cores on a rotary press, and continuously coating the tablet cores by a method as defined above.

The present invention also provides an apparatus for coating medicinal substrates of medicinal products with a dry powder, the apparatus including:

a conveying means, means for feeding substrates onto the conveying means, a feed for supplying dry powder to a region through which the conveying means passes, electric charging means for electrically charging the powder and/or the conveying means and/or the substrates such that the potential of the powder supplied to the region through which the conveying means passes is different from the potential of the substrates on the conveying means, means for treating dry powder coatings on the substrates to convert the powder into a fused film secured to the substrates.

The present invention also provides a medicinal product when coated by a method as described above and a medicinal product when produced by a method as described above.

BRIEF DESCRIPTION OF THE DRAWINGS

A method and apparatus for electrostatic coating of tablet cores will now be described by way of example with reference to the accompanying drawings of which.

DESCRIPTION OF PREFERRED EMBODIMENTS

Figure 1:
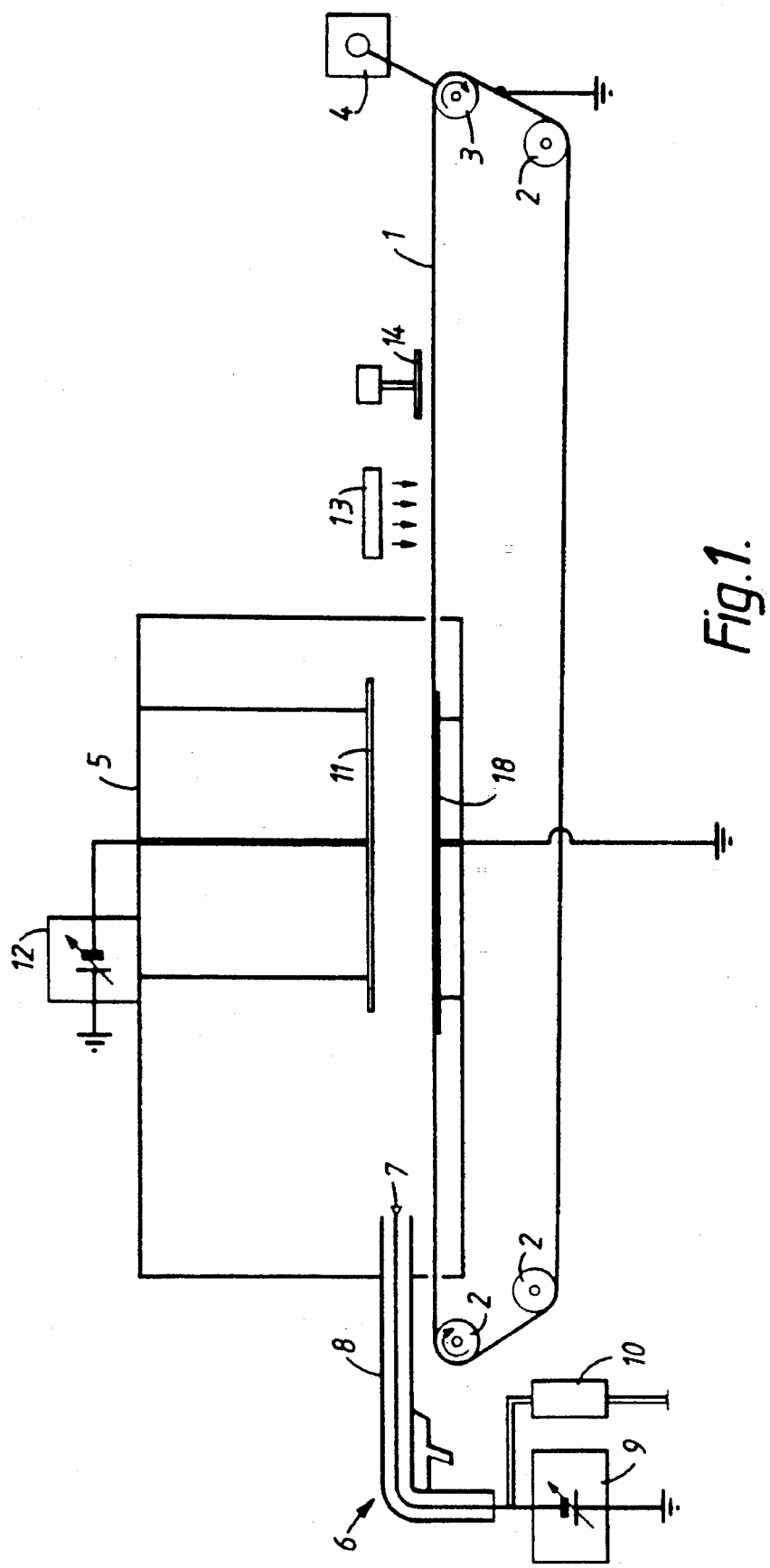
FIG. 1 is a schematic side view of an apparatus for coating tablets on one face.

The apparatus shown in FIG. 1 includes a conveyor belt 1 which is guided around three idler rollers 2 and a drive roller 3 driven by a motor 4 in the direction shown by an arrow in FIG. 1. A booth 5 is provided enclosing most of the upper run of the conveyor belt 1.

Apparatus for feeding tablet cores to the upstream end (the left hand end as seen in FIG. 1) of the conveyor belt 1 outside the booth 5 is provided, but is not shown in the drawing. The form of such apparatus is not part of the present invention. A feed 6 for supplying dry powder to the interior of the booth above the conveyor belt is also provided. In the example of the invention illustrated the feed 6 comprises an electrostatic powder gun employing a single fixed corona electrode 7 mounted at the end of the gun barrel 8 and connected to a voltage supply 9. A mixture of powder and air is fed to the gun barrel from a venturi powder feed 10.

Suspended from the top of the booth is an electrode 11 which is rectangular in plan view and extends across the whole width of the conveyor belt 1 and a portion of its length. The electrode 11 is connected to a voltage supply 12. Immediately below and supporting the conveyor belt 1 in the region below the electrode 11 is another rectangular electrode 18 which is connected to earth. The conveyor belt 1 is made of a laminate of polyvinylchloride and aluminium foil with the aluminium foil forming the outer layers of the belt and the belt is connected to earth.

An infra red heater 13 and a vibrating plate 14 are provided over the downstream end of the conveyor belt.

In use of the apparatus, pharmaceutical tablet cores are fed onto the upstream end of the belt 1 by a feed 6 and pass along the conveyor with one face of the core resting on the belt and the other facing upwards. Dry powder with which the tablet cores are to be coated is sprayed into the booth 5 by the spray gun 1 which charges the powder to a suitable potential (for this example it will be assumed that the powder is charged to a positive potential). Powder sprayed from the gun 1 enters the region between the electrode 11, which is maintained at a positive potential, and the conveyor belt 1 and electrode 18 both of which are earthed. Thus powder is directed downwardly away from the electrode 11 towards the conveyor belt 1 and the electrode 18. A coating of powder is therefore laid over the conveyor belt and the tablet cores on the conveyor belt.

The tablet cores are then passed under the infra red heater 13 which heats the coating of powder on the tablets sufficiently to cause the coating to melt and form a film coating over the upper side of the tablet core. As the tablets are carried beyond the heater 13 they are contacted by the vibrating plate 14 which evens out the coating. Thereafter, the film coating solidifies.

In order to provide a coating on the other side of the tablet core (if one is desired), the tablets are laid the other way up on a further conveyor arrangement similar to that shown in FIG. 1 and the process described above with respect to FIG. 1 is repeated. Apparatus for transferring tablets from one conveyor to another and for turning them over in the course of the transfer is already known (see for example FIGS. 2 and 3 of GB 1 075 404).

Figure 2:
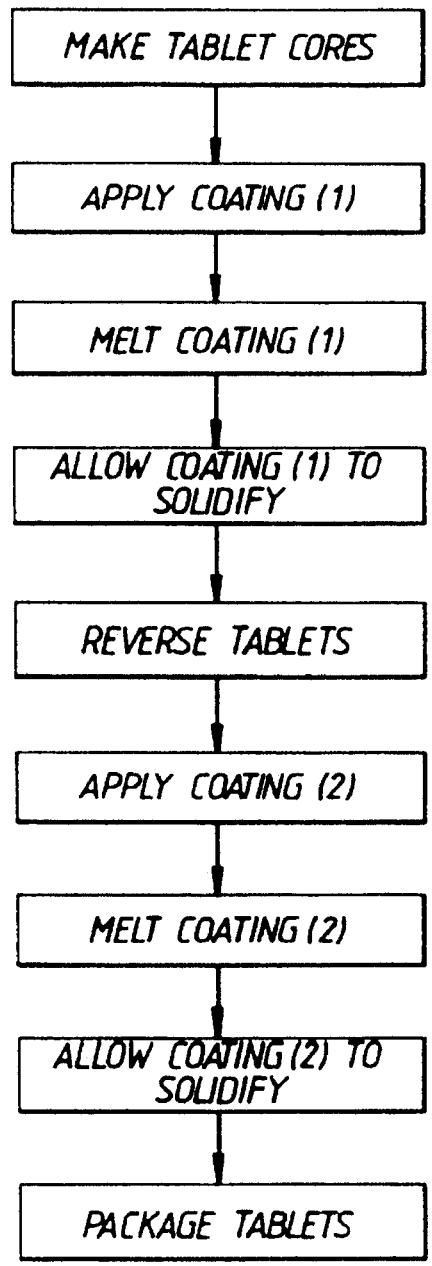
FIG. 2 is a block diagram of a continuous process for manufacturing coated tablets employing the apparatus of FIG. 1.

Referring now to FIG. 2, it will be seen that with the apparatus and method just described a continuous production of coated tablets can be provided. Tablet cores produced for example from a high speed rotary press are fed directly to the apparatus of FIG. 1 where their upper faces are coated with electrically charged dry powder. The dry powder coating is then melted by heating, the partially coated tablets allowed to cool and fed to another apparatus of the kind shown in FIG. 1 but with their uncoated faces now uppermost. Those uncoated faces are coated with electrically charged dry powder, the dry powder coating is melted by heating and the coated tablet allowed to cool and then fed to appropriate packaging machinery. Such a process can operate continuously.

Figure 3:
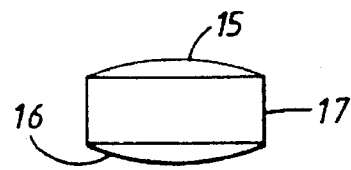
FIG. 3 is a side view of a coated tablet.

FIG. 3 shows a tablet having an upper face 15, a lower face 16, and a cylindrical side wall 17. In the first coating stage, one of the faces, say the face 15, is coated fully and the side wall 17 receives some powder coating but not a full coating. In the second coating stage the other face 16 is coated fully and the remainder of the coating to the side walls 17 is applied.

We claim:

1. A method of coating cores of pharmaceutical tablets with a dry powder, said method comprising the steps of:

feeding cores of pharmaceutical tablets onto a conveyor;

supplying dry powder to a region through which said cores are to be conveyed on said conveyor;

conveying the cores through said region with said cores supported by said conveyor and with said cores maintained at a different electric potential from that of said dry powder, whereby said dry powder is attracted to exposed surfaces of the cores to form partially coated cores having powder coatings thereon, and melting said dry powder coatings of the partially coated cores to convert the dry powder into fused film coatings secured to the cores, thereby forming partially coated cores.

2. A method according to claim 1, in which the method is carried out as a continuous process.

3. A method of according to claim 1, including the following further subsequent steps:

feeding said partially coated cores onto a further conveyor with the fused film coatings adjacent to the further conveyor and with that surface of the core that was adjacent to the conveyor during said conveying step exposed;

supplying further dry powder with which the exposed surfaces of the partially coated cores are to be coated to a region through which the further conveyor carrying the partially coated cores passes;

conveying the partially coated cores through the region with said partially coated cores supported by the further conveyor and with the partially coated cores maintained at a different electric potential from the dry powder, whereby the further dry powder is attracted to the exposed surfaces of the partially coated cores, and melting the further dry powder to convert the further dry powder into fused film coatings secured to the cores, thereby forming coated cores.

4. A method of according to claim 3, in which the further conveying conveyor carrying the partially coated cores is the same as the conveyor used for carrying the uncoated cores.

5. A method according to claim 1, in which the conveyor means comprises a conveyor belt.

6. A method according to claim 3, including a further mechanical treatment in which the depth of the coating over the surface of the coated cores is evened out.

7. A method according to claim 6, in which the evening out step is carried out by passing the coated cores under a vibrating plate or a rotating roller, the plate or roller contacting and evening out the coating on the coated cores.

8. A method according to claim 6, in which the evening out step is carried out by passing the coated cores under a jet of air.

9. A method according to claim 1, in which the powder is electrically charged.

10. A method according to claim 9, in which the powder is charged as it is supplied to the region through which the cores are to be conveyed on the conveyor.

11. A method according to claim 9, in which the charging is carried out using a corona charging apparatus.

12. A method according to claim 1, in which one or more electrodes maintained at a potential different from the potential in which the cores are maintained are provided above the conveyor in the region to which the dry powder is supplied.

13. A method according to claim 1, in which powder melted during said melting step has a particle size in the range of 1 µm to 1000 µm.

14. A method according to claim 1, in which the powder has a resistivity in the range of $10^6$ to $10^{24}$ Ωm.

15. A method according to claim 1, in which powder melted during said melting step has a viscosity of less than 500 Pas.

16. A method according to claim 1, in which the fused film has, after returning to the solid phase, a tensile strength of more than 0.5N/m$^2$.

17. A method according to claim 1, in which the powder has a melting point in the range of 50° C. to 180° C.

18. A method according to claim 17, in which the powder has a melting point in the range of 60° C. to 100° C.

19. A method according to claim 1, in which the cores are treated prior to application of the powder to make them electrically conducting.

20. A method according to claim 19, in which the treatment comprises moistening the exterior of the cores.

21. A method according to claim 1, in which the dry powder comprises at least one material selected from the group consisting of polyamides, polyalkenes, waxes, oils, polyesters, polyoxyethylenes, sugars, sugar alcohols and ethylene vinyl acetate copolymer.

22. A method according to claim 1, in which the dry powder comprises xylitol.

23. A method according to claim 1, in which the dry powder comprises polycaprolactone.

24. A method of coating cores of pharmaceutical tablets with a dry powder, said method comprising the steps of:

feeding cores of pharmaceutical tablets onto a conveying means;

supplying dry powder to a region through which said cores are to be conveyed on said conveying means;

conveying the cores through said region with said cores supported by said conveying means and with said cores maintained at a different electric potential from that of said dry powder, whereby said dry powder is attracted to exposed surfaces of the cores to form partially coated cores having powder coatings thereon;

melting said dry powder coatings of the partially coated cores to convert the dry powder into fused film coatings secured to the cores, thereby forming partially coated cores;

feeding said partially coated cores onto a further conveying means with the fused film coatings adjacent to the further conveying means and with that surface of the core that was adjacent to the conveying means during said conveying step exposed;

supplying further dry powder with which the exposed surfaces of the partially coated cores are to be coated to a region through which the further conveying means carrying the partially coated cores passes;

conveying the partially coated cores through the region with said partially coated cores supported by the further conveying means and with the partially coated cores maintained at a different electric potential from the dry powder, whereby the further dry powder is attracted to the exposed surfaces of the partially coated cores, and melting the further dry powder to convert the further dry powder into fused film coatings secured to the cores, thereby forming coated cores.

* * * * *